United States Patent [19]

Ancher et al.

[11] 4,368,199

[45] Jan. 11, 1983

[54] NOVEL DERIVATIVES OF 3,4,5-TRIMETHOXY CINNAMOYL PIPERAZINE, THEIR SALTS, THE PROCESS FOR PREPARING THE SAME AND THEIR APPLICATION IN THERAPEUTICS

[75] Inventors: Jean-Francois R. Ancher, Rueil Malmaison; Alain P. Lacour, La Varenne; Gerard H. Moinet, Orsay; Jacky A. Tisne-Versailles, Le Pecq, all of France

[73] Assignee: Delalande S.A., Courbevoie, France

[21] Appl. No.: 225,588

[22] Filed: Jan. 16, 1981

[30] Foreign Application Priority Data

Jan. 21, 1980 [FR] France .................................. 80 01242
Jan. 7, 1981 [FR] France .................................. 81 00178

[51] Int. Cl.$^3$ ............................................. C07D 241/02
[52] U.S. Cl. ..................................... 424/250; 542/439; 542/440
[58] Field of Search ................. 542/439, 440; 424/250

[56] References Cited

U.S. PATENT DOCUMENTS

| | | | |
|---|---|---|---|
| 3,590,034 | 6/1971 | Fauran et al. | 542/440 |
| 3,634,411 | 1/1972 | Fauran et al. | 542/440 |
| 3,753,984 | 8/1973 | Fauran et al. | 542/440 |
| 3,940,386 | 2/1976 | Slabo et al. | 542/440 |
| 4,016,154 | 4/1977 | Turin et al. | 542/440 |
| 4,029,650 | 6/1977 | Raynaud et al. | 542/440 |
| 4,178,442 | 12/1979 | Bourgery et al. | 542/439 |

FOREIGN PATENT DOCUMENTS

200149 4/1958 Austria .

OTHER PUBLICATIONS

Fauran et al., Chim Theapeutica, vol. 4, No. 4, 1969, pp. 290–293.

*Primary Examiner*—Arthur P. Demers
*Attorney, Agent, or Firm*—Flynn, Thiel, Boutell & Tanis

[57] ABSTRACT

1-substituted-4-(3,4,5-trimethoxy) cinnamoyl piperazine compounds are disclosed. The compounds exhibit a substantial activity of stimulating cardiac contractile force, without affecting the cardiac frequency, and they also exhibit coronary vasodilatory and hypotensive effects.

20 Claims, No Drawings

NOVEL DERIVATIVES OF 3,4,5-TRIMETHOXY CINNAMOYL PIPERAZINE, THEIR SALTS, THE PROCESS FOR PREPARING THE SAME AND THEIR APPLICATION IN THERAPEUTICS

The present invention relates to new derivatives of 3,4,5-trimethoxy cinnamoyl piperazine, the salts thereof and the process for preparing same and application thereof in therapeutics.

The new compounds correspond more exactly to the general formula:

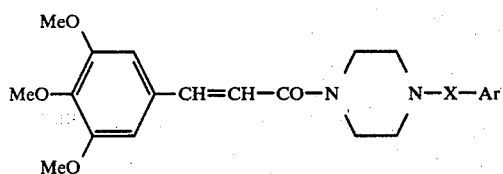

in which —X— represents:
either an alkylene radical —(CH$_2$)$_n$— wherein n assumes the value 1,2 or 3, a methylcarbonyl chain (—CH$_2$—CO—) or a 1-hydroxy ethyl chain

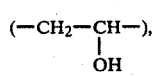

these two chains being bonded to the piperazine radical by their CH$_2$ group, in which cases Ar represents:
a phenyl radical of structure

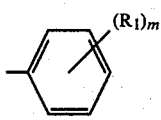

where m is either equal to 1 or 2, R$_1$ then representing a hydrogen atom, a halogen atom or an alkyl group of 1 to 5 carbon atoms, or is equal to 1, R$_1$ then representing an amino, nitro, alkylcarbonylamino, alkylsulfonylamino or alkylaminocarbonylamino group whose alkyl groups each comprise from 1 to 5 carbon atoms;
an aromatic radical of structure

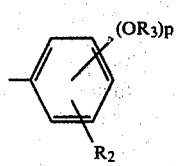

in which the set (R$_2$, R$_3$, p) assumes any one of the following values: (H, H, 1 or 2), (H, alkyl from 1 to 5 C, 1 or 2), (OH, H, 2), (OH, alkyl from 1 to 5 C, 1 or 2), (alkyloxy from 1 to 5 C, H, 2), (alkyloxy from 1 to 5 C, alkyl from 1 to 5 C, 2), (H, alkylcarbonyl from 2 to 5 C, 1 or 2);
the radicals of structures

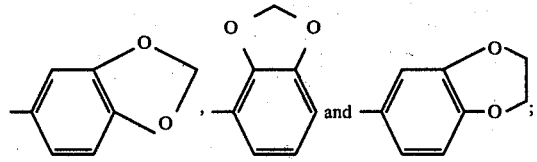

an aromatic radical of structure:

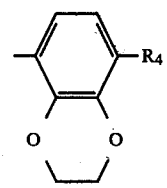

in which R$_4$ represents a hydroxy or alkyloxy group of 1 to 5 carbon atoms; or
a naphthyl nucleus;
or a chain of formula $$(-CH_2-CH_2-CO-), (-CH_2-CH_2-\underset{OH}{CH}-),$$

$$(-CH_2-\underset{OH}{CH}-CH_2-) \text{ or } (-CH_2-\underset{OH}{CH}-CH_2-OH),$$

bonded to the piperazine radical by the CH$_2$ group, in which cases Ar represents:
an aromatic group of structure

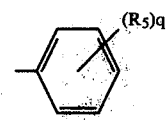

where R$_5$ represents a hydrogen or chlorine atom, or an alkyl group of 1 to 5 carbon atoms or an alkyloxy group of 1 to 5 carbon atoms and q assumes the value 1, 2 or 3;
an aromatic radical of structure:

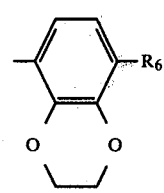

in which R$_6$ represents an alkyl group of 1 to 5 carbon atoms or an alkyloxy group of 1 to 5 carbon atoms;
the nuclei of structures:

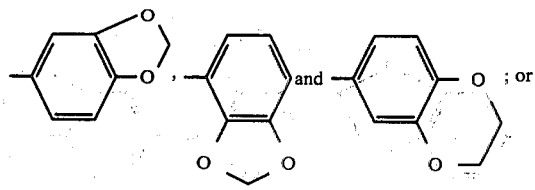

the naphthyl nucleus;

the —X—Ar chain being also able to be represented by the structure:

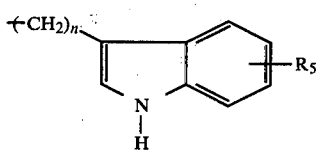

where n and R$_5$ have the same meanings as before, or the structure:

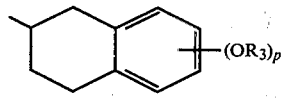

where p=1 or 2 and R$_3$ represents a hydrogen atom, an alkyl group of 1 to 5 carbon atoms or an alkylcarbonyl group of 2 to 5 carbon atoms.

As was mentioned above, the present invention also relates to the salts of the compounds of formula (I), which salts may be formed with pharmaceutically acceptable mineral acids, such as hydrochloric acid or organic acids such as oxalic acid.

In accordance with the present invention, the compounds of formula (I) are obtained by processes which differ depending on the meaning of the symbols X and Ar. Thus:

A. The compounds of formula (I) in which X represents an alkylene radical of structure (—CH$_2$)$_n$— in which n=1, 2 or 3, are obtained by condensation of 3,4,5-trimethoxy cinnamoyl piperazine of formula:

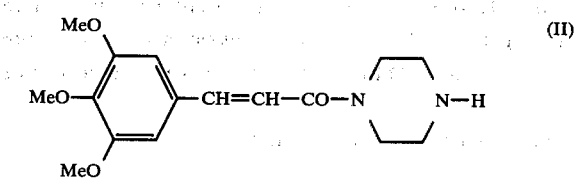

with the chlorides, bromides, tosylates or mesylates of formula:

$$Ar_1-(CH_2)_n-Y \qquad (III)$$

in which Y represents a chlorine or bromine atom or the tosyloxy or mesyloxy groups, n=1, 2 or 3 and Ar$_1$ has the same meaning as Ar in the formula (I) when X represents the alkylene group (—CH$_2$)$_n$—.

This condensation is preferably carried out at reflux in an organic solvent such as acetone, acetonitrile or DMF in the presence of a basic agent such as potassium carbonate.

B. The compounds of formula (I) in which X represents the —CH$_2$—CO— chain, except for the case where Ar represents the group of formula:

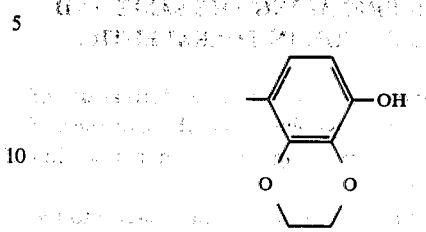

are obtained by condensation of the compound of formula (II) with the compounds of formula:

$$Ar_2-CO-CH_2-Y' \qquad (IV)$$

in which Y'=Cl or Br and Ar$_2$ has the same meaning as Ar$_1$ in formula (III), except for the values:

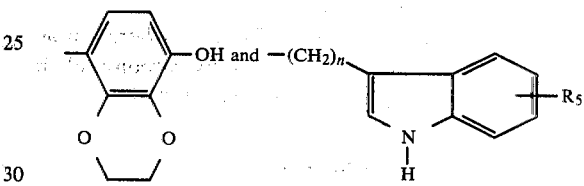

this condensation reaction being preferably carried out under the same conditions as the condensation of the compound of formula (II) with the compounds of formula (III).

The compound of formula (IV) having the particular form:

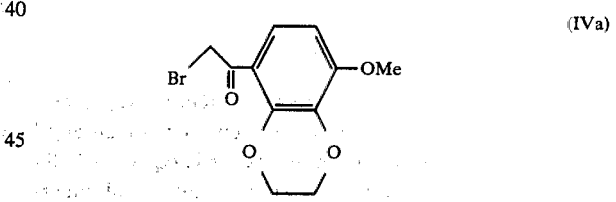

is new and it is obtained by action of cupric bromide in solution in a mixture of ethyl acetate and chloroform, on the compound of formula:

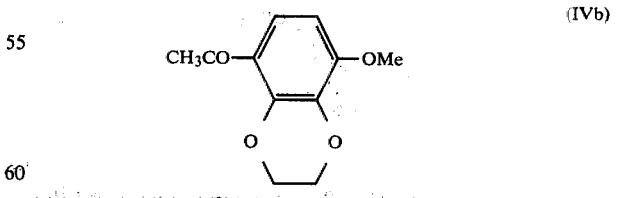

This latter is also new and is obtained by action of methyl sulfate, preferably in an acetone medium and in the presence of potassium carbonate, on 8-hydroxy 5-acetyl 1,4-benzodioxane.

The compound of formula (I) where the —X—Ar chain represents the

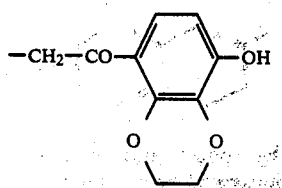

group is obtained by hydrolysis by means of potassium carbonate in a methanol medium of the compound of formula:

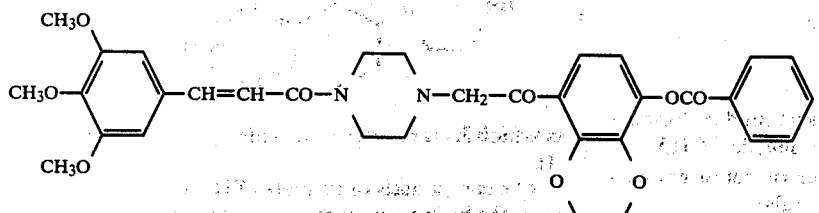

The compound of formula (Ia), which is new, is obtained by condensation of the compound of formula (II) with the compound of formula:

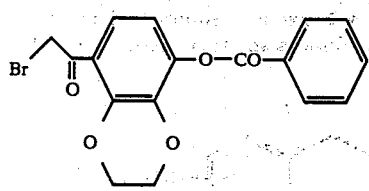
(IVc)

the operation method for carrying out this condensation being identical to that used for condensation of the compound of formula (II) with the compounds of formula (III).

The compound (IVc) is also new and is obtained by the process used for the synthesis of the compound of formula (IVa), but from the compound of formula:

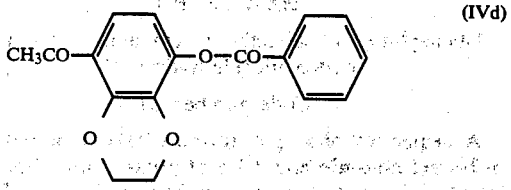
(IVd)

This latter is itself new and is obtained by action of benzyl chloride on 5-acetyl 8-hydroxy, 1,4-benzodioxane, in an organic solvent medium such as THF and in the presence of a base such as triethylamine.

C. The compounds of formula (I) in which X represents (—CH$_2$—CH$_2$—CO—) are obtained by reaction of the compound of formula (II) with the chlorhydrates of the compounds of formula:

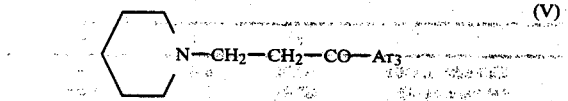
(V)

in which Ar$_3$ has the same meaning as Ar in formula (I) when X represents (—CH$_2$—CH$_2$—CO—).

This reaction is carried out preferably at reflux, in an alcohol solvent such as ethanol, isopropyl alcohol or butanol.

The compounds of formula (V) are obtained by so-called "MANNICH" reaction of piperidine with the compounds of formula:

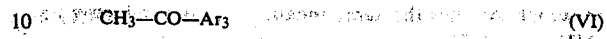
CH$_3$—CO—Ar$_3$  (VI)

in which Ar$_3$ has the same meanings as in formula (V).

D. The compounds (I) in which X represents the chains $$(-CH_2-CH-) \text{ and } (-CH_2-CH_2-CH-)$$
$$\quad\quad\;\; | \quad\quad\quad\quad\quad\quad\quad\quad\; |$$
$$\quad\quad\; OH \quad\quad\quad\quad\quad\quad\quad OH$$

are obtained by reduction, preferably by means of sodium borohydride, in the presence of NaOH and in an alcohol medium (preferably methanol), respectively of the compounds of formula (I) in which X represents the chain (—CH$_2$—CO—) and the chain (—CH$_2$—CH$_2$—CO—) prepared according to the processes set forth in points B and C above.

The compound of formula (I) in which the chain —X—Ar represents the

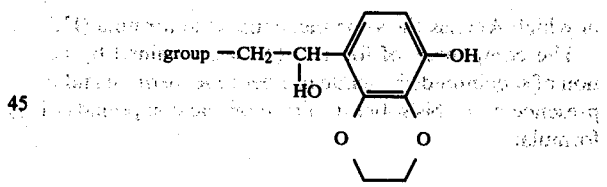

may also be obtained by reduction preferably by means of sodium in a methanol medium and in the presence of NaOh, of the compound (Ia).

E. The compounds of formula (I) in which X represents the chain

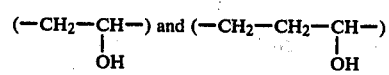

are obtained by condensation, preferably in an organic solvent such as acetonitrile, of the compound of formula (II) with those of formula:

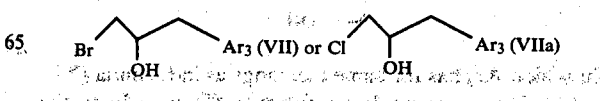

where Ar$_3$ has the same meanings as in formula (V).

The compounds of formula (VII) or (VIIa) are obtained by opening epibromhydrin or epichlorhydrin, in a T.H.F. medium and in the presence of cuprous iodide, by means of the magnesians of the compounds of formula

 Br—Ar₃     (VIII)

in which Ar₃ has the same meanings as in the formulae (VII) and (VIIa).

F. The compounds of formula (I) in which X represents the chain $$-CH_2-CH-CH_2OH,$$
$$|$$

are obtained by condensation of compound of formula (II), preferably in an acetone, acetonitrile, T.H.F. or D.M.F. medium and in the presence of potassium carbonate, with the compounds of formula:

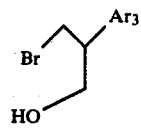 (IX)

in which Ar₃ has the same meanings as in formula (V).

The compounds of formula (IX) are obtained by saponification by means of potassium carbonate in a methanol medium of the compounds of formula:

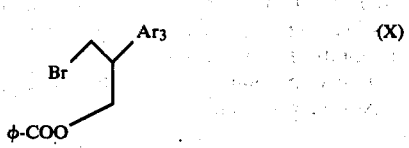 (X)

in which Ar₃ has the same meanings as in formula (IX).

The compounds of formula (X) are obtained by action of succinimide bromide in a benzene medium and in presence of azobisisobutyronitrile on the compounds of formula:

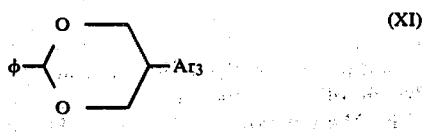 (XI)

in which Ar₃ has the same meanings as in formula (X).

The compounds of formula (XI) are themselves obtained by condensation of benzaldehyde in a benzene medium and in the presence of paratoluenesulfonic acid with the compounds of formula:

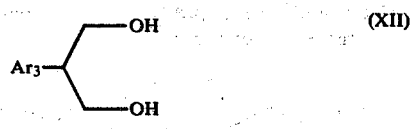 (XII)

in which Ar₃ has the same meanings as in formula (XI).

G. The compounds of formula (I) in which the —X—Ar chain is

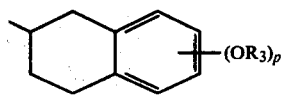

are obtained by condensation of the chloride of 3,4,5-trimethoxy cinnamoyl acid, preferably in a T.H.F. or D.M.F. medium and in the presence of triethylamine, on the compounds of formula:

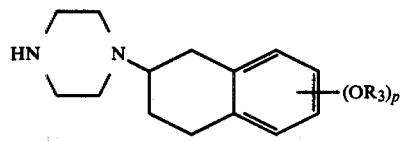 (XIII)

in which R₃ and p have the same meanings as in formula (I).

The compounds of formula (XIII) in which R₃ represents the hydrogen atom are obtained by demethylation by means of 48% bromhydric acid, of the compounds of formula (XIII) in which R₃ represents the methyl group.

The compounds of formula (XIII) in which R₃ represents an alkyl group of 1 to 5 carbon atoms are obtained by a two-step synthesis which consists in condensing piperazine in a benzene medium and in presence of paratoluene sulfonic acid with the compounds of formula:

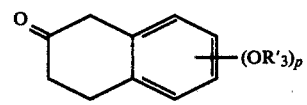 (XIV)

in which R'₃ represents an alkyl group of 1 to 5 carbon atoms and p=1 or 2, then in reducing the intermediate compounds thus formed, by means of sodium borohydride in an ethanol medium.

The following preparations are given by way of example to illustrate the invention.

EXAMPLE 1

1-benzyl-4-(3,4,5-trimethoxy) cinnamoyl piperazine hydrochloride hydrate (I)

Code number: 21

A suspension of 6.1 g of formula (II) compound, 3.2 g of benzyl chloride and 8.3 g of potassium carbonate in 70 ml of acetonitrile was brought to reflux for 5 hours. Then it was filtered, the filtrate diluted with 70 ml of acetone, chlorhydric ethanol was added, the precipitate was filtered and recrystallized in methanol. 4.8 g of the expected compound were isolated.

Yield: 56%
Melting point: 230° C.
Molecular weight: 440.14
Empirical formula: $C_{23}H_{29}ClN_2O_5 + 2/5\ H_2O$
Elementary analysis:

|  | C | H | N |
|---|---|---|---|
| Calculated (%) | 62.76 | 6.82 | 6.36 |
| Obtained (%) | 62.93 | 7.37 | 6.49 |

By the same process, but from the corresponding reagents, the compounds of formula (I) and of code numbers: 1 to 4, 22 to 57, 101 and 105 given in table I below were obtained.

EXAMPLE 2

2-[4-(3,4,5-trimethoxy) cinnamoyl piperazinyl]1-phenyl ethanone (I)

Code number: 58

A suspension of 15.4 g of formula (II) compound, 10 g of α-bromoacetophenone and 13.8 g of potassium carbonate in 100 ml of acetonitrile was brought to reflux for 30 minutes. Then it was filtered, the filtrate evaporated and the residue crystallized in isopropyl ether. Thus 17.7 g of the desired compound were isolated.
Yield: 84%
Melting point: 103° C.
Molecular weight: 424.48
Empirical formula: $C_{24}H_{28}N_2O_5$
Elementary analysis:

|  | C | H | N |
|---|---|---|---|
| Calculated (%) | 67.90 | 6.65 | 6.60 |
| Obtained (%) | 67.73 | 6.55 | 6.43 |

By the same process, but from the corresponding reagents, the compounds of formula (I) of code numbers: 5 to 10, 12, 59 to 78 given in table I below are obtained.

EXAMPLE 3

1-(3,4,5-trimethoxy phenyl) 3-[4'-(3,4,5-trimethoxy cinnamoyl) 1'-piperazinyl]propanone hydrochloride hydrate (I)

Code number: 99

A solution of 10.2 g of 3-piperidino 1-(3,4,5-trimethoxy)phenyl propanone (in chlorhydrate form) and 9 g of formula (II) compound in 30 ml of water and 30 ml of ethanol was brought to reflux for 8 hours. Then the solvents were evaporated, the residue taken up in chloroform, washed with water, dried on sodium sulfate, filtered, the filtrate was evaporated and the residue crystallized in ethanol (Melting point: 156° C.).

The precipitate was dissolved in ethanol, chlorhydric ethanol was added and the hydrochloride obtained was filtered.
Yield: 70%
Melting point: 162° C.
Molecular weight: 597.93
Empirical formula: $C_{28}H_{37}ClN_2O_8 + 5.5\%$ $H_2O$
Elementary analysis:

|  | C | H | N |
|---|---|---|---|
| Calculated (%) | 56.24 | 6.86 | 4.69 |
| Obtained (%) | 56.17 | 6.33 | 4.74 |

EXAMPLE 4

2-[4-(3,4,5-trimethoxy cinnamoyl) 1-piperazinyl]1-phenyl ethanol hydrochloride (I)

Code number: 79

A solution of 8.1 g of formula (I) compound, code number 58, described in example 2, in 200 ml of methanol and 0.1 ml of concentrated NaOH was brought to reflux, then 3.8 g of sodium borohydride were slowly added and left 1 hour at reflux. Then the solvent was evaporated, the residue taken up in ethyl acetate, washed with water, dried on sodium sulfate, filtered, the filtrate was evaporated, the residue dissolved in acetone, chlorhydric ethanol was added, diluted with ether and the precipitate obtained was filtered. 7.4 g of the expected compound were obtained.
Yield: 63%
Melting point: 226° C.
Molecular weight: 462.96
Empirical formula: $C_{24}H_{31}ClN_2O_5$
Elementary analysis:

|  | C | H | N |
|---|---|---|---|
| Calculated (%) | 62.26 | 6.75 | 6.05 |
| Obtained (%) | 62.07 | 6.71 | 6.01 |

By the same process, but from the corresponding reagents, the compounds of formula (I) of code numbers: 13 to 19, 80 to 98 and 100 appearing in table I below, were obtained.

EXAMPLE 5

3-[4-(3,4,5-trimethoxy cinnamoyl) 1-piperazinyl]1-(3,4-dimethoxy)phenyl 2-propanol hydrochloride hydrate (I)

Code number: 102

1st stage: 1-chloro 3-(3,4-dimethoxy) phenyl 2-propanol (VIIa)

To a suspension of 2.4 g of magnesium in the minimum of T.H.F. were added 21.7 g of 4-bromo-veratrole in 200 ml of T.H.F., while maintaining the reflux of the T.H.F. Then it was cooled to "40° C. and 0.2 g of CuI was added, stirring was carried out for 30 minutes and then 13.9 g of epichlorhydrin were slowly added. It was left to stir for 1 hour at 20° C., then washed with a saturated solution of ammonium chloride, dried on magnesium sulfate, filtered, the filtrate was evaporated and the residue distilled: $Eb_{0.05}$: 150°–152° C.

2nd stage: 3-[4-(3,4,5-trimethoxy cinnamoyl) 1-piperazinyl] 1-(3,4-dimethoxy)-phenyl-2-propanol hydrochloride hydrate (I)

Code number: 102

A suspension of 10 g of formula (VIIa) compound obtained in the preceding stage, 15.9 g of formula (II) compound, 6.4 g of sodium iodide and 17.8 g of potassium carbonate in 200 ml of acetonitrile was brought to reflux for 8 hours. Then it was filtered, the filtrate evaporated, the residue was taken up in methylene chloride, washed with water, dried on magnesium sulfate, filtered and the filtrate was evaporated. The raw product obtained was dissolved in ethanol, chlorhydric ethanol was added and the precipitate formed was filtered.
Yield: 30%
Melting point: 162° C.
Molecular weight: 546.88
Empirical formula: $C_{27}H_{37}ClNO_7 + 1.8\%$ $H_2O$
Elementary analysis:

|  | C | H | N |
|---|---|---|---|
| Calculated (%) | 59.29 | 7.02 | 5.13 |

-continued

|  | C | H | N |
| --- | --- | --- | --- |
| Obtained (%) | 59.21 | 7.03 | 5.02 |

By the same process, but from the corresponding reagents, the compounds of formula (I) of code numbers 20 and 103 given in table I below were obtained.

EXAMPLE 6

3-[4-(3,4,5-trimethoxy cinnamoyl) 1-piperazinyl] 2-phenyl 1-propanol hydrochloride hydrate (I)

Code number: 104

1st stage: 2,5-diphenyl 1,3-dioxanne (XI)

A solution of 85 g of 2-phenyl 1,3-propanediol, 59.3 g of benzaldehyde and 2 g of paratoluenesulfonic acid in 400 ml of benzene was brought to reflux for 6 hours, while removing the water formed. Then it was washed with water, dried on magnesium sulfate, filtered, the filtrate was evaporated and the residue crystallized in isopropyl ether. Thus, 84.7 g of the expected compound were obtained.

Yield: 63%
Melting point: 123° C.
Molecular weight: 240.29
Empirical formula: $C_{16}H_{16}O_2$
Elementary analysis

|  | C | H |
| --- | --- | --- |
| Calculated (%) | 79.97 | 6.71 |
| Obtained (%) | 79.89 | 6.54 |

2nd stage: 1-bromo 3-benzoyloxy 2-phenyl propane (X)

To a solution of 84 g of formula (XI) compound obtained in the preceding stage and 11.5 g of azobisisobutyronitrile in 400 ml of benzene were slowly added 68.4 g of succinimide bromide. Then it was left to agitate for an hour at ambient temperature then for 2 hours at reflux. Then it was diluted with ether, washed with water, the solvents were evaporated and the residue was chromatographed on a silica column (eluent:methylene chloride). 89 g were obtained (Yield: 79%) of an oily product.

3rd stage: 3-bromo 2-phenyl 1-propanol (IX)

A suspension of 16 g of the formula (X) compound obtained in the preceding stage and 1 g of potassium carbonate in 200 ml of methanol was left under agitation for 3 hours, then the mixture was brought to reflux for 2 hours, the methanol was evaporated, the residue was taken up in methylene chloride, washed with water, dried on magnesium sulfate, filtered, the filtrate was evaporated and the residue chromatographed on a silica column (eluent:heptane-ethyl acetate: 80–20). 5.9 g (Yield: 50%) of oily product were obtained.

4th stage: 3-[4-(3,4,5-trimethoxy cinnamoyl) 1-piperazinyl] 2-phenyl 1-propanol hydrochloride hydrate (I)

Code number: 104

A suspension of 28 g of formula (IX) compound obtained in the preceding stage, 30.6 g of compound (II) and 18 g of potassium carbonate in 300 ml of acetonitrile was brought to reflux for 5 hours. Then it was filtered, the filtrate evaporated, the residue was taken up in 1 N hydrochloric acid, washed with ether, basified by means of concentrated NaOH, extracted with ethyl acetate, washed with water, dried on sodium sulfate, filtered, the filtrate was evaporated, the residue was dissolved in ethyl acetate, chlorhydric ethanol was added, the precipitate formed (26 g) was filtered and recrystallized in ethyl acetate.

Yield: 45%
Melting point: 152° C.
Molecular weight: 492.30
Empirical formula: $C_{25}H_{33}ClN_2O_5 + 2\% \ H_2O$
Elementary analysis:

|  | C | H | N |
| --- | --- | --- | --- |
| Calculated (%) | 60.99 | 7.01 | 5.69 |
| Obtained (%) | 60.95 | 7.02 | 5.80 |

EXAMPLE 7

2-[4-(3,4,5-trimethoxy cinnamoyl) 1-piperazinyl] 1,2,3,4-tetrahydro 6,7-dihydroxy naphthyl hydrate (I)

A solution of 12.5 g of piperazine, 10 g of 6,7-dimethoxy 1,2,3,4-tetrahydro naphthalene 2-one and 1 g of paratoluenesulfonic acid in 200 ml of benzene was brought to reflux for 5 hours while removing the water formed. Then the solvent was evaporated, the residue was taken up in 200 ml of ethanol, 7.3 g of sodium borohydride were slowly added and the solution was brought up to reflux for one hour. Then the solvent was evaporated, the residue was taken up in chloroform, washed with water, dried on sodium sulfate, filtered, the filtrate was evaporated, the residue was dissolved in ethanol, chlorhydric ethanol was added and the precipitate formed was filtered. 9 g of the expected compound were obtained.

Yield: 68%
Melting point: >260° C.
Molecular weight: 349.29
Empirical formula: $C_{16}H_{26}Cl_2N_2O_2$
Elementary analysis:

|  | C | H | N |
| --- | --- | --- | --- |
| Calculated (%) | 55.01 | 7.21 | 8.02 |
| Obtained (%) | 54.83 | 7.43 | 8.04 |

By the same process, but from the corresponding reagents, 2-(1-piperazinyl) 5,6-dimethoxy 1,2,3,4-tetrahydro naphthyl-dihydrochloride (XIII) was obtained.

Melting point: >260° C.
Elementary analysis

|  | C | H | N |
| --- | --- | --- | --- |
| Calculated (%) | 55.01 | 7.50 | 8.02 |
| Obtained (%) | 54.90 | 7.86 | 7.98 |

2nd stage: 2-(1-piperazinyl) 6,7-dihydroxy 1,2,3,4-tetrahydro naphthyl dibromohydrate (XIII)

A solution of 7 g of formula (XIII) compound obtained in the preceding stage (in base form) in 200 ml of 48% bromhydric acid was brought to reflux for one hour. Then the solvents were evaporated and the residue crystallized in acetone.

Yield: 73%
Melting point: >260° C.
Empirical formula: $C_{14}H_{20}N_2O_2 + 2.25 \ HBr$ Elementary analysis:

|  | C | H | N |
|---|---|---|---|
| Calculated (%) | 37.88 | 5.39 | 6.31 |
| Obtained (%) | 37.86 | 5.35 | 6.60 |

By the same process, but from the corresponding reagents 2-(1-piperazinyl) 5,6-dihydroxy 1,2,3,4-tetrahydro naphthyl dibromhydrate (XIII) was obtained.
Melting point: >260° C.
Empirical formula: $C_{14}H_{20}N_2O_2 + 2\ HBr + 0.8\%\ H_2O$
Elementary analysis:

|  | C | H | N |
|---|---|---|---|
| Calculated (%) | 40.66 | 5.45 | 6.78 |
| Obtained (%) | 40.57 | 5.37 | 6.93 |

3rd stage: 2-[4-(3,4,5-trimethoxy cinnamoyl) 1-piperazinyl] 1,2,3,4-tetrahydro 6,7-dihydroxy naphthyl hydrate (I)

Code number: 108

To a suspension cooled to −20° C. of 5.8 g of formula (XIII) compound, prepared in the preceding stage, in 300 ml of D.M.F. and 7 g of triethylamine were added 6 g of 3,4,5-trimethoxy cinnamoic acid chloride and it was left under agitation for 30 minutes at −20° C. Then after 2 hours at ambient temperature, it was filtered, the filtrate was evaporated and the residue was chromatographed on a silica column, and eluted with the chloroform (90)—methanol (10) mixture. 27% of product was obtained.
Melting point: >260° C.
Molecular weight: 472.31
Empirical formula: $C_{26}H_{32}N_2O_6 + 0.8\%\ H_2O$
Elementary analysis:

|  | C | H | N |
|---|---|---|---|
| Calculated (%) | 66.12 | 6.91 | 5.93 |
| Obtained (%) | 65.77 | 7.03 | 5.90 |

By the same process, but from the corresponding reagents, the compounds of formula (I) of code numbers: 106, 107 and 109 given in table I below were obtained.

EXAMPLE 8

2-bromo 4'-methoxy 2',3'-ethylenedioxy acetophenone (IVa)

1st stage: 5-acetyl 8-methoxy 1,4-benzodioxane (IVb)
To a suspension of 39 g of 5-acetyl 8-hydroxy 1,4-benzodioxane and 55 g of potassium carbonate in 350 ml of acetone were slowly added 28.6 ml of dimethylsulfate. Then the reaction mixture was brought to reflux for 90 minutes, filtered, the filtrate was evaporated, the residue was taken up in chloroform, washed with water and with a 30% NaOH solution. Then it was dried on sodium sulfate, filtered, the solvent was evaporated and the product filtered on a silica column (eluent:ethyl ether). 33.1 g of the expected product were obtained.
Yield: 80%
Melting point: 67° C.
Molecular weight: 208.21
Empirical formula: $C_{11}H_{12}O_4$
Elementary analysis:

|  | C | H |
|---|---|---|
| Calculated (%) | 63.45 | 5.81 |
| Obtained (%) | 63.58 | 5.93 |

2nd stage: 2-bromo 4'-methoxy 2',3'-ethylene dioxy acetophenone (IVa)
To a suspension of 7.5 g of cupric bromide in 25 ml of ethyl acetate was slowly added a solution of 4.1 g of the compound (IVb) prepared in the preceding stage in 25 ml of chloroform. Then it was brought to reflux for 6 hours, filtered and the filtrate evaporated, the residue was taken up in chloroform and washed with a sodium bicarbonate solution then with water. It was dried on sodium sulfate, filtered and the filtrate evaporated. 4.2 g of the expected product were obtained (Yield: 73%—Melting point: 135° C.) which was immediately used in the synthesis of the corresponding compound (I), after thin layer chromatography verification.

EXAMPLE 9

2-[4-(3,4,5-trimethoxy cinnamoyl) 1-piperazinyl] (4'-hydroxy 2',3'-ethylene dioxy)acetophenone hydrochloride (I)

Code number: 11

1st stage: 5-acetyl 8-benzoyloxy 1,4-benzodioxane (IVd)
To a solution cooled to 0° C. of 80 g of 5-acetyl 8-hydroxy 1,4-benzodioxane and 72 ml of triethylamine in 500 ml of T.H.F. were slowly added 51.2 g of benzoyl chloride. Then it was left for 1 hour at room temperature, the solvent was evaporated, the residue was taken up in methylene chloride, washed with water, with dilute hydrochloric acid, then again with water and dried on sodium sulfate. It was filtered, the solvent was evaporated and 128 g of raw product were obtained (Yield~100%) which, after checking by thin film chromatography, was used in the following stage.

2nd stage: 4'-benzoyloxy 2',3'-ethylenedioxy 2-bromo acetophenone (IVc)
This product was obtained with a process identical to the one used in the 2nd stage of example 8, but from compound (IVd). The raw product obtained was purified by silica column chromatography (eluent:methylene chloride), then used immediately in the following stage.

3rd stage: 2-[4-(3,4,5-trimethoxy cinnamoyl) 1-piperazinyl] (4'-benzoyloxy 2',3'-ethylenedioxy)acetophenone hydrochloride trihydrate (Ia)
This compound was obtained with a process identical to the one used in example 2 for preparing compound (I) of code number 10, but from compound (IVc). The raw product obtained was dissolved in alcohol and 6,5 N chlorhydric ethanol was added, the precipitate formed was filtered and recrystallized in alcohol.
Yield: 40%
Melting point: 186° C.
Molecular weight: 693.13
Empirical formula: $C_{33}H_{35}ClN_2O_9$
Elementary analysis:

|  | C | H | N |
|---|---|---|---|
| Calculated (%) | 57.18 | 5.96 | 4.04 |

|  | C | H | N |
|---|---|---|---|
| Obtained (%) | 56.80 | 5.55 | 3.89 |

4th stage: 2-[4-(3,4,5-trimethoxy cinnamoyl) 1-piperazinyl] (4'-hydroxy 2',3'-ethylenedioxy)acetophenone hydrochloride (I)

A suspension of 15 g of the compound (Ia) obtained in the preceding stage and 0.005 g of potassium carbonate in 100 ml of methanol was agitated under a nitrogen flow, at room temperature, for 12 hours, then was brought to reflux for 3 hours, the methanol was evaporated, the residue was taken up in 2 N hydrochloric acid, washed with ethyl ether, then with ethyl acetate. It was alkalized with ammonia and extracted, the residue was dissolved in isopropyl alcohol and ~5.8 N chlorhydric ethanol was added and the precipitate obtained was filtered.

Thus, 12 g of the expected product were isolated.
Melting point: 213° C.
Molecular weight: 566.51
Empirical formula: $C_{26}H_{31}ClN_2O_8 + 1.75\ H_2O$
Elementary analysis:

|  | C | H | N |
|---|---|---|---|
| Calculated (%) | 55.12 | 5.96 | 4.95 |
| Obtained (%) | 55.00 | 5.87 | 4.69 |

TABLE I

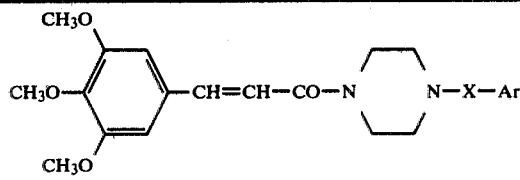

(I)

| Code Number | —X—Ar | Form | Empirical formula | Molecular weight | Melting point (°C.) | Yield (%) | ELEMENTARY ANALYSIS (%) C H N |
|---|---|---|---|---|---|---|---|
| 1 | —CH₂—(2-OCH₃-C₆H₄) | Chlorhydrate | $C_{24}H_{31}ClN_2O_5$ | 462.95 | 250 | 22 | Cal. 62.26 6.75 6.05 / Obt. 62.00 6.68 5.91 |
| 2 | —CH₂—(2,6-diOCH₃-C₆H₃) | Chlorhydrate | $C_{25}H_{33}ClN_2O_6$ | 492.99 | 218 | 14 | Cal. 60.90 6.75 5.68 / Obt. 60.84 6.89 5.54 |
| 3 | —CH₂—CH₂—(2-OH-C₆H₄) | Base | $C_{24}H_{30}N_2O_5$ | 426.49 | 175 | 38 | Cal. 67.58 7.09 6.57 / Obt. 67.34 7.21 6.61 |
| 4 | —CH₂—CH₂—(2,5-diOH-C₆H₃) | Hydrated Chlorhydrate | $C_{24}H_{30}N_2O_6$, HCl, 9/8 $H_2O$ | 499.23 | 252 | 16 | Cal. 57.74 6.71 5.61 / Obt. 57.99 6.33 5.84 |
| 5 | —CH₂—CO—(2-OH-C₆H₄) | di-chlorhydrate | $C_{24}H_{30}Cl_2N_2O_6$ | 513.41 | 220 | 25 | Cal. 56.14 5.89 5.46 / Obt. 56.21 5.58 5.36 |
| 6 | —CH₂—CO—(2,5-diOCH₃-C₆H₃) | oxalate | $C_{26}H_{32}N_2O_7$, (COOH)₂ | 574.57 | 172 | 60 | Cal. 58.53 5.96 4.88 / Obt. 58.59 5.43 4.65 |
| 7 | —CH₂—CO—(2,3,5-triOCH₃-C₆H₂) | hydrated chlorhydrate | $C_{27}H_{35}ClN_2O_8$, $H_2O$ | 569.04 | 148 | 22 | Cal. 56.99 6.55 4.92 / Obt. 56.81 6.45 4.87 |
| 8 | —CH₂—CO—(2,3,5-triOCH₃-C₆H₂) | hydrated chlorhydrate | $C_{27}H_{35}ClN_2O_8$, 1/1 $H_2O$ | 570.84 | 188 | 75 | Cal. 56.81 6.57 4.91 / Obt. 57.14 6.42 4.93 |
| 9 | —CH₂—CO—(2,5-diOH-C₆H₃) | hydrated base | $C_{24}H_{28}N_2O_7$, 4/5 $H_2O$ | 470.89 | 134 | 43 | Cal. 61.21 6.34 6.14 / Obt. 61.31 6.20 5.92 |

TABLE I-continued $$\text{(CH}_3\text{O)}_3\text{-C}_6\text{H}_2\text{-CH=CH-CO-N}\underset{\phantom{xx}}{\overset{\phantom{xx}}{\bigcirc}}\text{N-X-Ar} \quad \text{(I)}$$

| Code Number | —X—Ar | Form | Empirical formula | Molecular weight | Melting point (°C.) | Yield (%) | ELEMENTARY ANALYSIS (%) C H N |
|---|---|---|---|---|---|---|---|
| 10 | —CH$_2$—CO—(3,4-ethylenedioxy-2-methoxyphenyl) | base | C$_{27}$H$_{32}$N$_2$O$_8$ | 512.54 | 175 | 80 | Cal. 63.27 6.29 5.47<br>Obt. 63.09 6.33 5.44 |
| 11 | —CH$_2$—CO—(3,4-ethylenedioxy-2-hydroxyphenyl) | hydrated chlorhydrate | C$_{26}$H$_{31}$ClN$_2$O$_8$, 1.75 H$_2$O | 566.51 | 213 | 71 | Cal. 55.12 5.96 4.95<br>Obt. 55.00 5.87 4.69 |
| 12 | —CH$_2$CO—C$_6$H$_4$—NH—SO$_2$CH$_3$ | hydrated base | C$_{25}$H$_{31}$N$_3$O$_7$, 2/5 H$_2$O | 524.79 | 240 | 67 | Cal. 57.21 6.11 8.01<br>Obt. 57.47 6.38 8.21 |
| 13 | —CH$_2$—CH(OH)—C$_6$H$_4$—OH | chlorhydrate | C$_{24}$H$_{31}$ClN$_2$O$_6$ | 478.96 | 254 | 74 | Cal. 60.18 6.52 5.85<br>Obt. 59.82 6.61 6.03 |
| 14 | —CH$_2$—CH(OH)—C$_6$H$_3$(OCH$_3$)$_2$ | hydrated chlorhydrate | C$_{26}$H$_{35}$ClN$_2$O$_7$, 7/6 H$_2$O | 544.03 | 150 | 54 | Cal. 57.40 6.92 5.15<br>Obt. 57.90 7.04 5.02 |
| 15 | —CH$_2$—CH(OH)—C$_6$H$_2$(OCH$_3$)$_3$ (2,3,4-trimethoxy) | hydrated base | C$_{27}$H$_{36}$N$_2$O$_8$, 11/10 H$_2$O | 536.39 | 137 | 74 | Cal. 60.45 7.18 5.22<br>Obt. 60.16 6.98 5.23 |
| 16 | —CH$_2$—CH(OH)—C$_6$H$_2$(OCH$_3$)$_3$ (3,4,5-trimethoxy) | hydrated chlorhydrate | C$_{27}$H$_{37}$ClN$_2$O$_8$, 5/4 H$_2$O | 575.56 | 195 | 50 | Cal. 56.34 6.92 4.87<br>Obt. 56.21 6.87 4.92 |
| 17 | —CH$_2$—CH(OH)—C$_6$H$_3$(OH)$_2$ | hydrated chlorhydrate | C$_{24}$H$_{30}$N$_2$O$_7$, HCl, ½ H$_2$O | 499.46 | 216 | 50 | Cal. 57.71 6.36 5.60<br>Obt. 57.40 6.61 5.61 |
| 18 | —CH$_2$—CH(OH)—(ethylenedioxyphenyl-OH) | hydrated chlorhydrate | C$_{26}$H$_{33}$ClN$_2$O$_8$, ⅝ H$_2$O | 549.01 | 190 | 82 | Cal. 56.87 6.30 5.10<br>Obt. 57.20 6.25 4.90 |
| 19 | —CH$_2$—CH(OH)—C$_6$H$_4$—NHSO$_2$CH$_3$ | hydrated base | C$_{25}$H$_{33}$N$_3$O$_7$S, 0.55 H$_2$O | 529.51 | 222 | 31 | Cal. 56.70 6.49 7.94<br>Obt. 56.43 6.67 8.15 |
| 20 | —CH$_2$—CH(OH)—CH$_2$—C$_6$H$_5$ | chlorhydrate | C$_{25}$H$_{33}$ClN$_2$O$_5$ | 476.99 | 148 | 35 | Cal. 60.88 7.11 5.68<br>Obt. 61.08 7.14 5.49 |

TABLE I-continued $$\text{(CH}_3\text{O)}_3\text{-C}_6\text{H}_2-\text{CH}=\text{CH}-\text{CO}-\text{N}\underset{\underset{}{\diagdown}}{\diagup}\text{N}-\text{X}-\text{Ar} \qquad (I)$$

| Code Number | —X—Ar | Form | Empirical formula | Molecular weight | Melting point (°C.) | Yield (%) | ELEMENTARY ANALYSIS (%) C H N |
|---|---|---|---|---|---|---|---|
| 21 | —CH$_2$—C$_6$H$_5$ | HCl + 2/5 H$_2$O | C$_{23}$H$_{29}$ClN$_2$O$_5$ + 2/5 H$_2$O | 440.14 | 230 | 56 | Cal. 62.76 6.82 6.36<br>Obt. 62.93 7.37 6.49 |
| 22 | —CH$_2$—C$_6$H$_4$—Cl | HCl | C$_{23}$H$_{28}$Cl$_2$N$_2$O$_4$ | 467.38 | 218 | 59 | Cal. 59.10 6.04 5.99<br>Obt. 59.40 6.32 5.97 |
| 23 | —CH$_2$—C$_6$H$_4$—F | Hydrated hydrochloride | C$_{23}$H$_{28}$ClFN$_2$O$_4$ + ½ H$_2$O | 450.93 | 213 | 96 | Cal. 60.45 6.32 6.13<br>Obt. 60.51 6.53 6.21 |
| 24 | —CH$_2$—C$_6$H$_4$(o-Cl) | Base | C$_{23}$H$_{27}$ClN$_2$O$_4$ | 430.92 | 128 | 64 | Cal. 64.10 6.32 6.50<br>Obt. 64.02 6.49 6.41 |
| 25 | —CH$_2$—C$_6$H$_4$(o-CH$_3$) | Base | C$_{24}$H$_{30}$N$_2$O$_4$ | 410.49 | 130 | 59 | Cal. 70.22 7.37 6.82<br>Obt. 70.37 7.56 6.74 |
| 26 | —CH$_2$—C$_6$H$_4$(m-OCH$_3$) | HCl | C$_{24}$H$_{31}$ClN$_2$O$_5$ | 462.95 | 246 | 37 | Cal. 62.26 6.75 6.05<br>Obt. 61.99 6.90 5.91 |
| 27 | —CH$_2$—C$_6$H$_4$—OCH$_3$ | Hydrated Hydrochloride | C$_{24}$H$_{31}$ClN$_2$O$_5$ + ¼ H$_2$O | 462.96 | 226 | 67 | Cal. 61.66 6.79 5.99<br>Obt. 61.75 6.78 5.82 |
| 28 | —CH$_2$-(3,4-methylenedioxyphenyl) | Hydrated Hydrochloride | C$_{24}$H$_{29}$ClN$_2$O$_6$ + ⅜ H$_2$O | 488.96 | 239 | 83 | Cal. 58.95 6.15 5.73<br>Obt. 59.11 6.24 5.89 |
| 29 | —CH$_2$—C$_6$H$_3$(OCH$_3$)(OH) | Base | C$_{24}$H$_{30}$N$_2$O$_6$ | 442.49 | 206 | 46 | Cal. 65.14 6.83 6.33<br>Obt. 65.19 6.95 6.34 |
| 30 | —CH$_2$—C$_6$H$_2$(OCH$_3$)$_3$ (3,4,5) | Hydrated Sulfate | C$_{26}$H$_{36}$N$_2$O$_{11}$S + ¾ H$_2$O | 598.14 | 130 | 10 | Cal. 52.20 6.32 4.68<br>Obt. 52.23 6.75 4.39 |
| 31 | —CH$_2$—C$_6$H$_2$(OCH$_3$)$_3$ | Hydrated Methane-Sulfonate | C$_{27}$H$_{38}$N$_2$O$_{10}$S + ½ H$_2$O | 588.66 | 170 | 61 | Cal. 55.09 6.62 4.76<br>Obt. 54.99 6.68 4.80 |
| 32 | —CH$_2$—C$_6$H$_2$(OCH$_3$)$_3$ | Hydrated Base | C$_{26}$H$_{34}$N$_2$O$_7$ + ½ H$_2$O | 495.56 | 128 | 26 | Cal. 63.01 7.12 5.65<br>Obt. 62.70 7.26 5.50 |

TABLE I-continued (I)

$$CH_3O-\underset{\underset{CH_3O}{|}}{\overset{\overset{CH_3O}{|}}{C_6H_2}}-CH=CH-CO-N\underset{\diagdown\diagup}{\overset{\diagup\diagdown}{}}N-X-Ar$$

| Code Number | —X—Ar | Form | Empirical formula | Molecular weight | Melting point (°C.) | Yield (%) | ELEMENTARY ANALYSIS (%) C  H  N |
|---|---|---|---|---|---|---|---|
| 33 | —CH₂—C₆H₂(OCH₃)₂OH (2,6-diOCH₃, 4-OH via CH₂) | Hydrated Methane-Sulfonate | C₂₆H₃₆N₂O₁₀S + 2/5 H₂O | 575.836 | 245 | 32 | Cal. 54.22 6.44 4.87<br>Obt. 54.48 6.42 4.90 |
| 34 | —CH₂—C₆H₄—OH (o) | Base | C₂₃H₂₈N₂O₅ | 412.47 | 173 | 23 | Cal. 66.97 6.84 6.79<br>Obt. 66.85 7.18 6.66 |
| 35 | —CH₂—C₆H₄—OH (m) | Base | C₂₃H₂₈N₂O₅ | 412.47 | 182 | 12 | Cal. 66.97 6.84 6.79<br>Obt. 66.66 6.98 6.73 |
| 36 | —CH₂—C₆H₄—OH (p) | Base | C₂₃H₂₈N₂O₅ | 412.47 | 225 | 18 | Cal. 66.97 6.84 6.79<br>Obt. 66.80 6.79 6.45 |
| 37 | —CH₂—C₆H₄—NHSO₂CH₃ | HCl | C₂₄H₃₂ClN₃O₆S | 526.04 | 220 | 44 | Cal. 54.79 6.13 7.99<br>Obt. 54.58 6.14 7.94 |
| 38 | —CH₂—C₆H₄—NH—CONHCH₃ | Base | C₂₅H₃₂N₄O₅ | 468.54 | 160 | 36 | Cal. 64.08 6.88 11.96<br>Obt. 63.80 7.15 11.84 |
| 39 | —CH₂—C₆H₄—NO₂ | Hydrated Sulfate | C₂₃H₂₉N₃O₁₀S + 1/6 H₂O | 542.55 | 250 | 80 | Cal. 50.91 5.45 7.75<br>Obt. 51.18 5.22 7.74 |
| 40 | —CH₂—C₆H₄—NH₃ | Hydrated diHCl | C₂₃H₃₁Cl₂N₃O₄ + 1.25 H₂O | 506.94 | 230 | 60 | Cal. 54.49 6.66 8.29<br>Obt. 54.53 6.60 8.31 |
| 41 | —CH₂—C₆H₄—NHCOCH₃ | Hydrated Oxalate | C₂₇H₃₃N₃O₉ + 3/5 H₂O | 554.37 | 150 | 30 | Cal. 58.49 6.22 7.58<br>Obt. 58.16 6.29 7.50 |
| 42 | —CH₂—C₆H₃(OH)₂ | Base | C₂₃H₂₈N₂O₆ | 428.47 | 217 | 25 | Cal. 64.47 6.59 6.54<br>Obt. 64.35 6.88 6.38 |
| 43 | —CH₂—CH₂—C₆H₅ | Hydrated Hydrochloride | C₂₄H₃₁ClN₂O₄ + ½ H₂O | 452.97 | 188 | 26 | Cal. 63.63 7.05 6.19<br>Obt. 63.63 7.26 6.33 |
| 44 | —CH₂—CH₂—C₆H₄—Cl | Hydrated Hydrochloride | C₂₄H₃₀Cl₂N₂O₄ + 2/5 H₂O | 488.62 | 218 | 74 | Cal. 58.99 6.35 5.73<br>Obt. 58.92 6.23 5.77 |
| 45 | —CH₂—CH₂—C₆H₄—F | HCl | C₂₄H₃₀ClFN₂O₄ | 464.95 | 219 | 33 | Cal. 61.99 6.50 6.03<br>Obt. 61.86 6.53 6.00 |
| 46 | —CH₂—CH₂—C₆H₄—OCH₃ | Hydrated Hydrochloride | C₂₅H₃₃ClN₂O₅ + 1/5 H₂O | 480.59 | 219 | 73 | Cal. 62.48 7.00 5.83<br>Obt. 62.47 6.94 5.98 |

TABLE I-continued $$\text{(I)}$$

Structure: 3,4,5-trimethoxyphenyl—CH=CH—CO—N(piperazine)N—X—Ar

| Code Number | —X—Ar | Form | Empirical formula | Molecular weight | Melting point (°C.) | Yield (%) | ELEMENTARY ANALYSIS (%) C H N |
|---|---|---|---|---|---|---|---|
| 47 | —CH$_2$—CH$_2$—(3-OCH$_3$-phenyl) | Base | C$_{25}$H$_{32}$N$_2$O$_5$ | 440.55 | 90 | 56 | Cal. 68.16 7.32 6.36<br>Obt. 68.32 7.49 6.51 |
| 48 | —CH$_2$—CH$_2$—(4-OCH$_3$-phenyl) | Base | C$_{25}$H$_{32}$N$_2$O$_5$ | 440.55 | 137 | 35 | Cal. 68.16 7.32 6.36<br>Obt. 68.03 7.56 6.12 |
| 49 | —CH$_2$—CH$_2$—(2,3-diOCH$_3$-phenyl) | Oxalate | C$_{28}$H$_{36}$N$_2$O$_{10}$ | 560.58 | 200 | 42 | Cal. 59.99 6.47 5.00<br>Obt. 59.95 6.64 5.07 |
| 50 | —CH$_2$—CH$_2$—(2,3,4-triOCH$_3$-phenyl) | HCl | C$_{27}$H$_{37}$ClN$_2$O$_7$ | 537.04 | 230 | 46 | Cal. 60.38 6.94 5.22<br>Obt. 60.08 7.04 5.03 |
| 51 | —CH$_2$—CH$_2$—(2-HO-phenyl) | Hydrated Base | C$_{24}$H$_{30}$N$_2$O$_5$ + 1/6 H$_2$O | 429.49 | 177 | 20 | Cal. 67.11 7.12 6.52<br>Obt. 66.88 7.11 6.28 |
| 52 | —CH$_2$—CH$_2$—(4-OH-phenyl) | Hydrated Hydrochloride | C$_{24}$H$_{31}$ClN$_2$O$_5$ + H$_2$O | 480.98 | 250 | 10 | Cal. 59.93 6.92 5.82<br>Obt. 59.65 6.66 5.52 |
| 53 | —CH$_2$—CH$_2$—(4-NHSO$_2$CH$_3$-phenyl) | Base | C$_{25}$H$_{33}$N$_3$O$_6$S | 503.60 | 214 | 50 | Cal. 59.62 6.61 8.34<br>Obt. 59.32 6.76 8.08 |
| 54 | —CH$_2$—CH$_2$—(4-NHCONHCH$_3$-phenyl) | Base | C$_{26}$H$_{34}$N$_4$O$_5$ | 482.56 | 220 | 72 | Cal. 64.71 7.10 11.61<br>Obt. 64.52 7.23 11.42 |
| 55 | —CH$_2$—CH$_2$—(4-NO$_2$-phenyl) | Hydrated Hydrochloride | C$_{24}$H$_{30}$ClN$_3$O$_6$ + H$_2$O | 509.98 | 200 | 85 | Cal. 56.52 6.32 8.24<br>Obt. 56.54 6.19 8.22 |
| 56 | —CH$_2$—CH$_2$—(4-NH$_2$-phenyl) | Hydrated diHCl | C$_{24}$H$_{33}$Cl$_2$N$_3$O$_4$ + H$_2$O | 516.46 | >260 | 96 | Cal. 55.81 6.83 8.14<br>Obt. 56.10 6.72 8.11 |
| 57 | —CH$_2$—CH$_2$—(4-NHCOCH$_3$-phenyl) | Base | C$_{26}$H$_{33}$N$_3$O$_5$ | 467.55 | 191 | 54 | Cal. 66.79 7.11 8.99<br>Obt. 66.30 7.30 8.65 |
| 58 | —CH$_2$—CO—phenyl | Base | C$_{24}$H$_{28}$N$_2$O$_5$ | 424.48 | 103 | 84 | Cal. 67.90 6.65 6.60<br>Obt. 67.73 6.55 6.43 |
| 59 | —CH$_2$—CO—(4-Cl-phenyl) | Base | C$_{24}$H$_{27}$ClN$_2$O$_5$ | 458.93 | 135 | 70 | Cal. 62.81 5.93 6.10<br>Obt. 62.77 5.90 6.14 |
| 60 | —CH$_2$—CO—(4-F-phenyl) | Hydrated Oxalate | C$_{26}$H$_{29}$FN$_2$O$_9$ + ½ H$_2$O | 544.52 | 134 | 45 | Cal. 57.35 5.62 5.15<br>Obt. 57.22 5.43 5.14 |
| 61 | —CH$_2$—CO—(3,4-diCl-phenyl) | HCl | C$_{24}$H$_{27}$Cl$_3$N$_2$O$_5$ | 529.84 | 212 | 40 | Cal. 54.40 5.14 5.29<br>Obt. 52.88 5.08 5.22 |

TABLE I-continued $$\text{(I)} \quad \underset{CH_3O}{\underset{|}{\overset{CH_3O}{\overset{|}{\bigcirc}}}}-CH=CH-CO-N\underset{\phantom{X}}{\bigcirc}N-X-Ar$$

| Code Number | —X—Ar | Form | Empirical formula | Molecular weight | Melting point (°C.) | Yield (%) | ELEMENTARY ANALYSIS (%) C H N |
|---|---|---|---|---|---|---|---|
| 62 | —CH$_2$—CO—(2-naphthyl) | Base | C$_{28}$H$_{30}$N$_2$O$_5$ | 474.54 | 121 | 68 | Cal. 70.87 6.37 5.90<br>Obt. 70.66 6.48 5.72 |
| 63 | —CH$_2$—CO—(2-CH$_3$O-phenyl) | Base | C$_{25}$H$_{30}$N$_2$O$_6$ | 454.51 | 146 | 83 | Cal. 66.06 6.65 6.16<br>Obt. 66.04 6.79 5.88 |
| 64 | —CH$_2$—CO—(3-OCH$_3$-phenyl) | Hydrated Hydrochloride | C$_{25}$H$_{31}$ClN$_2$O$_6$ + ½ H$_2$O | 499.97 | 136 | 10 | Cal. 60.05 6.57 5.71<br>Obt. 60.02 6.95 6.06 |
| 65 | —CH$_2$—CO—(4-OCH$_3$-phenyl) | Base | C$_{25}$H$_{30}$N$_2$O$_6$ | 454.51 | 113 | 94 | Cal. 66.06 6.65 6.16<br>Obt. 65.76 6.47 6.13 |
| 66 | —CH$_2$—CO—(3,4-methylenedioxyphenyl) | HCl | C$_{25}$H$_{29}$ClN$_2$O$_7$ | 504.95 | 260 | 20 | Cal. 59.46 5.79 5.55<br>Obt. 59.26 5.80 5.51 |
| 67 | —CH$_2$—CO—(4-OH-3-OCH$_3$-phenyl) | Hydrated Hydrochloride | C$_{25}$H$_{31}$ClN$_2$O$_7$ + 1.75 H$_2$O | 538.49 | 198 | 32 | Cal. 55.76 6.46 5.20<br>Obt. 55.31 6.09 5.06 |
| 68 | —CH$_2$—CO—(3,5-diOCH$_3$-phenyl) | Hydrated Hydrochloride | C$_{26}$H$_{33}$ClN$_2$O$_7$ + 3/5 H$_2$O | 531.81 | 208 | 84 | Cal. 58.72 6.48 5.27<br>Obt. 58.88 6.38 5.34 |
| 69 | —CH$_2$—CO—(3,4-diOCH$_3$-phenyl) | Hydrated Hydrochloride | C$_{26}$H$_{33}$ClN$_2$O$_7$ + 1/5 H$_2$O | 524.60 | 214 | 79 | Cal. 59.52 6.42 5.34<br>Obt. 59.61 6.50 5.32 |
| 70 | —CH$_2$—CO—(2,5-diOCH$_3$-phenyl) | Hydrated Hydrochloride | C$_{26}$H$_{33}$ClN$_2$O$_7$ + 3/5 H$_2$O | 531.81 | 210 | 67 | Cal. 58.72 6.48 5.27<br>Obt. 58.63 6.29 5.18 |
| 71 | —CH$_2$—CO—(2,3-diOCH$_3$-phenyl) | Hydrated Hydrochloride | C$_{26}$H$_{33}$ClN$_2$O$_7$ + 1% H$_2$O | 526.26 | 225 | 62 | Cal. 59.34 6.43 5.33<br>Obt. 59.00 6.76 5.13 |
| 72 | —CH$_2$—CO—(2,6-diOCH$_3$-phenyl) | Hydrated Hydrochloride | C$_{26}$H$_{33}$ClN$_2$O$_7$ + 3.5% H$_2$O | 539.89 | 158 | 59 | Cal. 57.84 6.53 5.19<br>Obt. 57.53 6.53 5.34 |

TABLE I-continued (I)

$$CH_3O\text{-}C_6H_2(OCH_3)_2\text{-}CH=CH\text{-}CO\text{-}N(\text{piperazine})N\text{-}X\text{-}Ar$$

| Code Number | —X—Ar | Form | Empirical formula | Molecular weight | Melting point (°C.) | Yield (%) | ELEMENTARY ANALYSIS (%) C H N |
|---|---|---|---|---|---|---|---|
| 73 | —CH$_2$—CO—(2,4,5-trimethoxyphenyl) | Hydrated Hydrochloride | C$_{27}$H$_{35}$ClN$_2$O$_8$ + 1% H$_2$O | 556.59 | 205 | 52 | Cal. 58.26 6.45 6.03 Obt. 58.25 6.55 5.03 |
| 74 | —CH$_2$—CO—(2-hydroxyphenyl) | hemi-oxalate | C$_{25}$H$_{29}$N$_2$O$_8$ | 485.49 | 212 | 57 | Cal. 61.84 6.02 5.77 Obt. 61.34 6.18 5.74 |
| 75 | —CH$_2$—CO—(4-hydroxyphenyl) | Hydrated Base | C$_{24}$H$_{28}$N$_2$O$_6$ + 4/5 H$_2$O | 454.89 | 190 | 40 | Cal. 63.36 6.56 6.16 Obt. 63.28 6.89 6.03 |
| 76 | —CH$_2$—CO—(4-NHCONHCH$_3$-phenyl) | Hydrated Base | C$_{26}$H$_{32}$N$_4$O$_6$ + 1.1% H$_2$O | 502.07 | 128 | 65 | Cal. 62.20 6.55 11.16 Obt. 61.89 6.58 11.06 |
| 77 | —CH$_2$—CO—(3,5-dihydroxyphenyl) | Hydrated Base | C$_{24}$H$_{28}$N$_2$O$_7$ + ¾ H$_2$O | 469.99 | 245 | 54 | Cal. 61.32 6.33 5.96 Obt. 60.99 6.37 5.91 |
| 78 | —CH$_2$—CO—(1,4-benzodioxan-6-yl) | HCl | C$_{26}$H$_{31}$ClN$_2$O$_7$ | 518.98 | 220 | 58 | Cal. 60.17 6.02 5.40 Obt. 59.82 6.25 5.58 |
| 79 | —CH$_2$—CH(OH)—phenyl | HCl | C$_{24}$H$_{31}$ClN$_2$O$_5$ | 462.96 | 226 | 63 | Cal. 62.26 6.75 6.05 Obt. 62.07 6.71 6.01 |
| 80 | —CH$_2$—CH(OH)—(4-Cl-phenyl) | HCl | C$_{24}$H$_{30}$Cl$_2$N$_2$O$_5$ | 497.41 | 208 | 60 | Cal. 57.95 6.08 5.63 Obt. 57.67 5.77 5.65 |
| 81 | —CH$_2$—CH(OH)—(4-F-phenyl) | Hydrated Hydrochloride | C$_{24}$H$_{30}$ClFN$_2$O$_5$ + ¼ H$_2$O | 485.46 | 200 | 69 | Cal. 59.37 6.33 5.77 Obt. 59.40 6.17 5.68 |
| 82 | —CH$_2$—CH(OH)—(3,4-diCl-phenyl) | Base | C$_{24}$H$_{28}$Cl$_2$N$_2$O$_5$ | 495.39 | 118 | 42 | Cal. 58.18 5.70 5.66 Obt. 58.30 5.64 5.65 |
| 83 | —CH$_2$—CH(OH)—(2-naphthyl) | HCl | C$_{28}$H$_{33}$ClN$_2$O$_5$ | 513.02 | 221 | 70 | Cal. 65.55 6.48 5.46 Obt. 65.34 6.52 5.48 |
| 84 | —CH$_2$—CH(OH)—(2-OCH$_3$-phenyl) | Hydrated Hydrochloride | C$_{25}$H$_{33}$ClN$_2$O$_6$ + 1/5 H$_2$O | 496.59 | 194 | 67 | Cal. 60.46 6.78 5.64 Obt. 60.50 6.73 5.29 |
| 85 | —CH$_2$—CH(OH)—(3-OCH$_3$-phenyl) | Hydrated Hydrochloride | C$_{25}$H$_{33}$ClN$_2$O$_6$ + ¼ H$_2$O | 498.99 | 220 | 63 | Cal. 60.17 6.80 5.61 Obt. 60.16 6.82 5.74 |

TABLE I-continued (I) Structure: $CH_3O$-, $CH_3O$-, $CH_3O$- substituted phenyl—CH=CH—CO—N(piperazine)N—X—Ar

| Code Number | —X—Ar | Form | Empirical formula | Molecular weight | Melting point (°C.) | Yield (%) | ELEMENTARY ANALYSIS (%) C H N |
|---|---|---|---|---|---|---|---|
| 86 | —CH$_2$—CH(OH)—C$_6$H$_4$—OCH$_3$ | HCl | C$_{25}$H$_{33}$ClN$_2$O$_6$ | 492.99 | 218 | 65 | Cal. 60.90 6.75 5.68 / Obt. 60.83 6.49 5.63 |
| 87 | —CH$_2$—CH(OH)—C$_6$H$_3$(OH)(OCH$_3$) | Base | C$_{25}$H$_{32}$N$_2$O$_7$ | 472.52 | 197 | 50 | Cal. 63.54 6.83 5.93 / Obt. 63.44 6.85 5.66 |
| 88 | —CH$_2$—CH(OH)—C$_6$H$_3$(OCH$_3$)$_2$ | Hydrated Hydrochloride | C$_{26}$H$_{35}$ClN$_2$O$_7$ + 2/5 H$_2$O | 537.51 | 156 | 83 | Cal. 58.09 6.75 5.21 / Obt. 58.19 7.13 5.10 |
| 89 | —CH$_2$—CH(OH)—C$_6$H$_3$(OCH$_3$)$_2$ | Hydrated Hydrochloride | C$_{26}$H$_{35}$ClN$_2$O$_7$ + 1/10 H$_2$O | 524.21 | 210 | 79 | Cal. 59.50 6.76 5.34 / Obt. 59.30 7.01 5.37 |
| 90 | —CH$_2$—CH(OH)—C$_6$H$_3$(OCH$_3$)$_2$ | Hydrated Hydrochloride | C$_{26}$H$_{35}$ClN$_2$O$_7$ + 9/40 H$_2$O | 527.07 | 230 | 80 | Cal. 59.24 6.69 5.31 / Obt. 58.84 6.69 5.25 |
| 91 | —CH$_2$—CH(OH)—C$_6$H$_3$(OCH$_3$)$_2$ | Hydrated Hydrochloride | C$_{26}$H$_{35}$ClN$_2$O$_7$ + 1% H$_2$O | 528.29 | 196 | 69 | Cal. 59.10 6.79 5.31 / Obt. 58.97 6.81 5.26 |
| 92 | —CH$_2$—CH(OH)—C$_6$H$_3$(OCH$_3$)$_2$ | Hydrated Hydrochloride | C$_{26}$H$_{35}$ClN$_2$O$_7$ + 2% H$_2$O | 533.69 | 164 | 55 | Cal. 58.51 6.86 5.25 / Obt. 58.30 6.62 5.22 |
| 93 | —CH$_2$—CH(OH)—C$_6$H$_4$—OH | Hydrated Base | C$_{24}$H$_{30}$N$_2$O$_6$ + ½ H$_2$O | 451.50 | 142 | 58 | Cal. 63.84 6.92 6.21 / Obt. 64.03 6.42 6.17 |
| 94 | —CH$_2$—CH(OH)—C$_6$H$_4$—OH | Hydrated Hydrochloride | C$_{24}$H$_{31}$ClN$_2$O$_6$ + ½ H$_2$O | 487.97 | 236 | 27 | Cal. 59.07 6.61 5.74 / Obt. 59.30 6.82 5.62 |
| 95 | —CH$_2$—CH(OH)—C$_6$H$_4$—NHCONHCH$_3$ | Hydrated Hydrochloride | C$_{26}$H$_{35}$ClN$_4$O$_6$ + 2.5% H$_2$O | 548.58 | 198 | 38 | Cal. 56.92 6.71 10.21 / Obt. 56.62 6.46 10.09 |
| 96 | —CH$_2$—CH(OH)—C$_6$H$_3$(OH)$_2$ | Hydrated Base | C$_{24}$H$_{30}$N$_2$O$_7$ + 1.25 H$_2$O | 481.02 | 148 | 42 | Cal. 59.92 6.81 5.82 / Obt. 59.67 6.36 5.74 |

TABLE I-continued $$\text{(I)}$$

Structure: 3,4,5-trimethoxyphenyl-CH=CH-CO-N(piperazine)N-X-Ar

| Code Number | —X—Ar | Form | Empirical formula | Molecular weight | Melting point (°C.) | Yield (%) | ELEMENTARY ANALYSIS (%) C H N |
|---|---|---|---|---|---|---|---|
| 97 | —CH₂—CH(OH)—(2-OCH₃, 3,4-ethylenedioxyphenyl) | Hydrated Hydrochloride | $C_{27}H_{35}ClN_2O_8$ + 2/5 $H_2O$ | 551.02 | 210 | 55 | Cal. 58.09 6.46 5.02 / Obt. 57.61 6.91 4.83 |
| 98 | —CH₂—CH(OH)—(2,3-propylenedioxyphenyl) | Base | $C_{26}H_{32}N_2O_7$ | 484.53 | 158 | 67 | Cal. 64.45 6.66 5.78 / Obt. 64.17 6.65 5.71 |
| 99 | —CH₂—CH₂—CO—(3,4,5-trimethoxyphenyl) | Hydrated Hydrochloride | $C_{28}H_{37}ClN_2O_8$ + 5.5% $H_2O$ | 597.93 | 162 | 70 | Cal. 56.24 6.86 4.69 / Obt. 56.17 6.33 4.74 |
| 100 | —CH₂—CH₂—CH(OH)—(3,4,5-trimethoxyphenyl) | Hydrated Hydrochloride | $C_{28}H_{39}ClN_2O_8$ + 4.4% $H_2O$ | 593.16 | 145 | 70 | Cal. 56.69 7.12 4.72 / Obt. 56.42 6.85 4.74 |
| 101 | —CH₂—CH₂—CH₂—(3,4,5-trimethoxyphenyl) | Hydrated Hydrochloride | $C_{28}H_{39}ClN_2O_7$ + 1.9 $H_2O$ | 585.29 | 144 | 25 | Cal. 57.47 7.37 4.79 / Obt. 57.46 6.57 4.88 |
| 102 | —CH₂—CH(OH)—CH₂—(3,4-dimethoxyphenyl) | Hydrated Hydrochloride | $C_{27}H_{37}ClNO_7$ + 1.8% $H_2O$ | 546.88 | 162 | 30 | Cal. 59.29 7.02 5.13 / Obt. 59.21 7.03 5.02 |
| 103 | —CH₂—CH(OH)—CH₂—(3,4,5-trimethoxyphenyl) | Hydrated Hydrochloride | $C_{28}H_{39}ClN_2O_8$ + 3.1% $H_2O$ | 585.15 | 156 | 28 | Cal. 57.47 7.07 4.79 / Obt. 57.73 7.12 4.38 |
| 104 | —CH₂—CH(CH₂—OH)—phenyl | Hydrated Hydrochloride | $C_{25}H_{33}ClN_2O_5$ + 2% $H_2O$ | 492.30 | 152 | 45 | Cal. 60.99 7.01 5.69 / Obt. 60.95 7.02 5.80 |
| 105 | —CH₂—CH₂—(indol-3-yl) | HCl | $C_{26}H_{32}ClN_3O_4$ | 485.99 | 252 | 37 | Cal. 64.25 6.64 8.65 / Obt. 63.99 6.94 8.35 |
| 106 | 6,7-dimethoxy-1,2,3,4-tetrahydronaphthalen-2-yl | Hydrated Base | $C_{28}H_{36}N_2O_6$ + $H_2O$ | 514.60 | 116 | 46 | Cal. 65.35 7.44 5.44 / Obt. 65.39 7.64 5.76 |
| 107 | 5,6-dimethoxy-1,2,3,4-tetrahydronaphthalen-2-yl | Hydrated Hydrochloride | $C_{28}H_{37}ClN_2O_6$ + 0.3% $H_2O$ | 534.65 | >260 | 61 | Cal. 62.90 7.01 5.24 / Obt. 62.82 7.27 5.26 |

TABLE I-continued $$CH_3O\text{-}C_6H_2(OCH_3)_2(OCH_3)\text{-}CH=CH\text{-}CO\text{-}N\underset{\diagdown}{\diagup}\overset{\diagdown}{\diagup}N\text{-}X\text{-}Ar \quad (I)$$

| Code Number | —X—Ar | Form | Empirical formula | Molecular weight | Melting point (°C.) | Yield (%) | ELEMENTARY ANALYSIS (%) C  H  N |
|---|---|---|---|---|---|---|---|
| 108 | tetralinyl-OH, OH (3,4) | Hydrated Base | $C_{26}H_{32}N_2O_6$ + 0.8% $H_2O$ | 472.31 | >260 | 27 | Cal. 66.12 6.91 5.93<br>Obt. 65.77 7.03 5.90 |
| 109 | tetralinyl-OH, OH (1,2) | Hydrated Hydrochloride | $C_{26}H_{33}ClN_2O_6$ + 1.2% $H_2O$ | 511.03 | >260 | 34 | Cal. 61.10 6.82 5.48<br>Obt. 60.80 7.15 5.21 |

The compounds of formula (I) were studied on laboratory animals and showed cardiac contractile force stimulating properties, without activity on the cardiac frequency, as well as coronarian vasodilatory and hypotensive properties.

Tests were carried out on dogs anaesthetized with sodic pentobarbital (30 mg/kg/i.v.) and the compounds of formula (I) were administered intravenously. The activity on the cardiac contractile force was measured with a BRODIE and WALTON stress gauge fixed to the left ventricle.

The arterial pressure was measured at the femoral artery with a SANBORN pressure sensor.

The cardiac frequency was automatically counted by means of a cardiotachymeter from the pulse pressure wave.

The coronary flow was measured by means of an electromagnetic probe of the STATHAM or BIOTRONEX type at the coronary artery.

The acute toxicity was assessed in accordance with the MILLER and TAINTER method (Proc. Sci. Exp. Biol. Med. 1944, 57, 261)

To illustrate the invention some results obtained with the compounds of formula (I) are given in table II below.

TABLE II

| Tested Compounds | LD 50 (mouse) (mg/kg/i.v.) | Administered dose (dog) (mg/kg/i.v.) | Variation of the average arterial pressure (%) | Duration (mn) | Variation of the cardiac frequency (%) | Duration (mn) | Increase of the coronary flow (%) | Duration (mn) | Increase of the cardiac contractile force (%) | Duration (mn) |
|---|---|---|---|---|---|---|---|---|---|---|
| 2 | 105 | 0.625 | −12 | 1 to 20 | +6 | <5 | +93 | <20 | +71 | 5 to 30 |
|  |  | 2.5 | −25 | 1 to 20 | +8 | 1 to 40 | +76 to +398 | >30 | +58 to +278 | >30 |
| 3 | >200 | 0.625 | −9 | 1 to 30 | 0 |  | +26 | 5 | +47 | 30 |
|  |  | 2.5 | −36 | >30 | +7 | 5 to 30 | +62 | 5 to 10 | +62 | 5 to 30 |
| 7 | 1000 | 0.625 | −22 | 5 to 30 | −2 to +15 | 5 to 30 | +277 | <5 | +69 | 15 to 30 |
|  | (p.o. 0%) | 2.5 | −35 | 15 to 30 | −8 to +9 | 5 to 30 | +416 | <20 | +51 | <10 |
| 10 | 180 | 0.625 | −7 | <5 | +2 | <5 | +39 | 1 to 15 | +9 | <10 |
|  |  | 2.5 | −16 | >30 | +12 | >30 | +46 | 20 to 30 | +53 | 10 |
| 41 | >200 | 2.5 | −36 | 21 to 40 | −16 | 0 to 30 | — | — | +35 | 20 to 30 |
| 54 | >200 | 2.5 | −9 | 20 to 30 | +4 | 0 to 30 | +181 | 10 to 30 | +48 | 5 to 30 |
| 62 | 45 | 2.5 | −14 | 10 | +4 | 5 | — | — | +43 | >30 |
| 70 | 168 | 2.5 | −21 | 20 to 30 | +5 | 0 to 20 | +27 | 10 to 20 | +50 | 5 to 10 |
| 89 | >100 | 2.5 | −38 | >30 | −10 | 0 to 30 | — | — | +51 | 0 to 30 |
| 90 | 1000 (p.o. 80%) | 2.5 | −11 | 20 to 30 | 0 |  | +15 | 15 to 30 | +42 | 5 to 20 |
| 95 | >200 | 2.5 | −20 | 20 to 30 | +8 | 1 to 30 | +27 | 10 to 20 | +21 | 10 |
| 102 | >200 | 2.5 | −26 | >30 | −4 | 1 to 5 | +34 | 15 to 30 | +13 | 10 |
| 105 | >200 | 2.5 | −34 | >30 | 0 |  | +55 | 1 to 30 | +17 | 1 to 10 |
| 108 | 200 (20%) | 2.5 | −20 | >30 | +3 | 0 to 5 | +29 | 5 to 20 | +44 | 5 to 20 |

As can be seen from the results given in table II, the compounds of formula (I) have a substantial stimulating activity on the cardiac contractile force with no (or little) activity on the cardiac frequency as well as coronary vasodilator and hypotensive effects.

Because of these properties and because of their low toxicity, the compounds of the invention find their application in therapeutics and they will be used in particular in the treatment of troubles due to cardiac deficiency.

They will be administered, alone or in combination, possibly associated with pharmaceutically acceptable vehicles, either orally, in the form of pills, tablets or capsules, in doses up to 200 mg/day (taken at one or several times), or intravenously, in the form of an injectable phial, in doses up to 25 mg/day.

We claim:
1. A compound having the formula

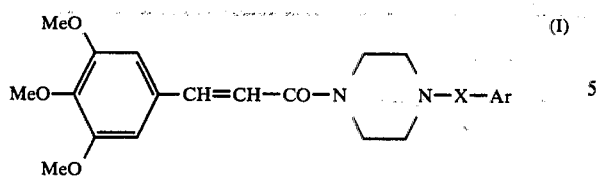 (I)

in which (A) —X— represents either —(CH$_2$)$_n$— in which n is 1, 2 or 3, or —CH$_2$—CO—, these two chains being bonded to the piperazine nucleus by their respective CH$_2$ group, and Ar represents:

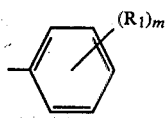 (1)

in which m is 1 or 2, and when m is 1, R$_1$ is hydrogen, halogen, alkyl, amino, nitro, alkylcarbonylamino, alkylsulfonylamino or alkylaminocarbonylamino wherein the respective alkyls each have from 1 to 5 carbon atoms, and when m is 2, R$_1$ is hydrogen, halogen or alkyl having from 1 to 5 carbon atoms;

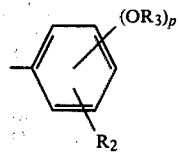 (2)

in which the set (R$_2$, R$_3$, p) has any one of the following values: (H,H, 1 or 2), (H, alkyl from 1 to 5 C, 1 or 2), (OH, H, 2), (OH, alkyl from 1 to 5 C, 1 or 2), (alkoxy having 1 to 5 C, H, 2), (alkoxy having 1 to 5 C, alkyl from 1 to 5 C, 2), (H, alkylcarbonyl from 2 to 5 C, 1 or 2);

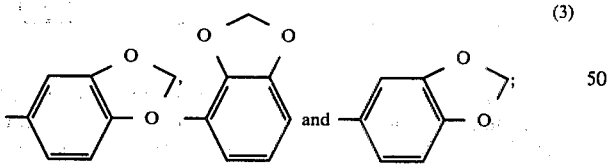 (3)

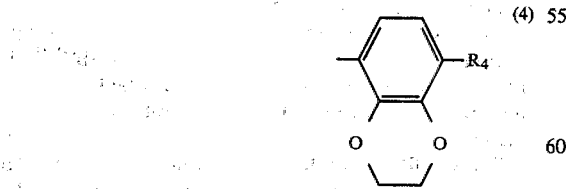 (4)

in which R$_4$ is hydroxy or alkoxy having 1 to 5 carbon atoms; or (5) naphthyl; or (B) —X— represents —CH$_2$—CH$_2$—CO—, bonded to the piperazine nucleus by the CH$_2$ group, and Ar represents:

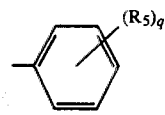 (1)

in which R$_5$ is hydrogen, chlorine, alkyl having 1 to 5 carbon atoms or an alkoxy having 1 to 5 carbon atoms, and q is 1, 2 or 3;

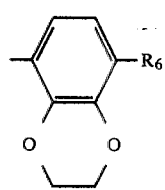 (2)

in which R$_6$ is alkyl having 1 to 5 carbon atoms or alkoxy having 1 to 5 carbon atoms;

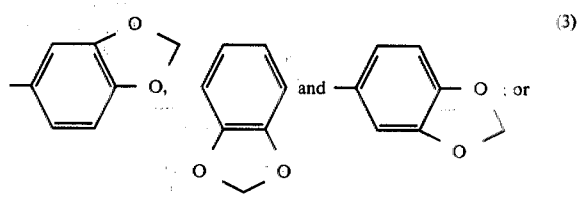 (3)

(4) naphthyl nucleus; or

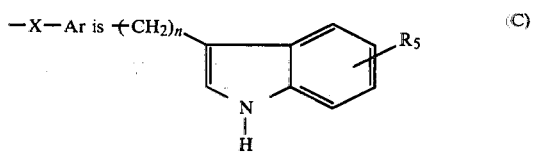 (C)

in which n and R$_5$ have the same meanings as defined above, or

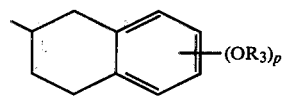

in which p is 1 or 2 and R$_3$ is hydrogen, alkyl group having 1 to 5 carbon atoms or alkylcarbonyl having 2 to 5 carbon atoms, and pharmacologically acceptable salts thereof.

2. A compound according to claim 1, wherein X is (—CH$_2$—)$_n$ and Ar is:

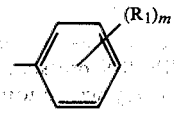

wherein when n is 1, (R$_1$)$_m$ is H, 4—Cl, 4—F, 2—Cl, 2—CH$_3$, 4—NHSO$_2$CH$_3$, 4—NHCONHCH$_3$, 4—NO$_2$, 4—NH$_2$ or 4—NHCOCH$_3$; and when n is 2, (R$_1$)$_m$ is H, 4—Cl, 4—F, 4—NHSO$_2$CH$_3$, 4—NHCONHCH$_3$, 4—NO$_2$, 4—NH$_2$ or 4—NHCOCH$_3$.

3. A compound according to claim 1, wherein X is —CH$_2$CO— and Ar is:

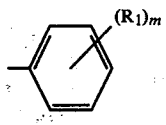

wherein (R₁)ₘ is 4—NHSO₂CH₃, H, 4—Cl, 4—F, 3,4—diCl or 4—NHCONHCH₃.

4. A compound according to claim 1, wherein X is —(—CH₂—)ₙ and Ar is:

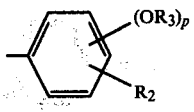

wherein when n is 1, [R₂, (OR₃)ₚ] is [H,2—OCH₃], [H,3,4—diOCH₃], [H,3—OCH₃], [H,4—OCH₃], [4—OH,3—OCH], [2—OCH₃, 4,6—diOCH₃], [2—OCH₃, 3,4—diOCH₃], [3—OCH₃4,5—diOCH₃], [4—OH, 3,5—diOCH₃], [H,2—OH], [H,3—OH], [H,4—OH] or [H, 3,4—diOH]; when n is 2, [R₂, (OR₃)ₚ] is [H, 3—OH], [H,3,4—diOH], [H, 2—OCH₃], [H,3—OCH₃], [H,4—OCH₃], [H, 3,4—diOCH₃], [3—OCH₃, 4,5—diOCH₃], [H, 2—OH] or [H,4—OH]; and when n is 3, [R₂, (OR₃)ₚ] is [3—OCH₃, 4,5—diOCH₃].

5. A compound according to claim 1, wherein X is —CH₂CO— and Ar is:

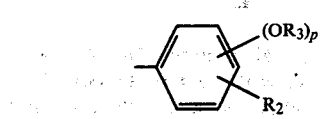

wherein [R₂, (OR₃)ₚ] is [H,3—OH], [H, 3,4—diOCH₃], [2—OCH₃, 3,4—diOCH₃], [3—OCH₃, 4,5—diOCH₃], [H, 3,4—diOH], [H,2—OCH₃], [H, 3—OCH₃], [H, 4—OCH₃], [4—OH, 3—OCH₃], [H,3,5—diOCH₃], [H, 2,4—diOCH₃], [H, 2,5—diOCH₃], [H, 2,6—diOCH₃], [H, 2,3—diOCH₃], [2—OCH₃, 4,6—diOCH₃], [H, 2—OH], [H, 4—OH] or [H, 3,5—diOH].

6. A compound according to claim 1, wherein X is —CH₂CO— and Ar is:

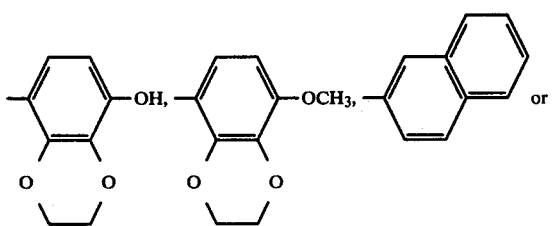

7. A compound according to claim 1, wherein:

(a) X is —CH₂— or —CH₂CO—, and Ar is 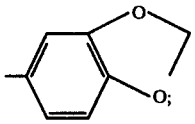

(b) X is —CH₂—CH₂—CO—, and Ar is 3,4,5—tri OCH₃ phenyl group.

8. A compound according to claim 1, wherein —X—Ar is

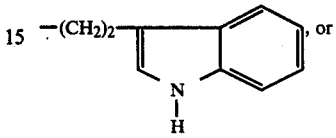

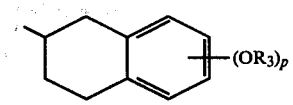

wherein (OR₃)ₚ is 6,7—diOCH₃, 6,7—diOH, 5,6—diOCH₃ or 5,6—diOH.

9. A compound having the formula

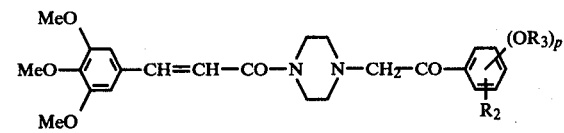

in which the set (R₂, R₃, p) is selected from the group consisting of (H, H, 1 or 2), (H, alkyl having 1 to 5 carbons, 1 or 2), (OH, H, 2), (OH, alkyl having 1 to 5 carbons, 1 or 2), (alkoxy having from 1 to 5 carbons, H, 2), (alkoxy having from 1 to 5 carbons, alkyl having from 1 to 5 carbons, 2), (H, alkylcarbonyl having from 2 to 5 carbons, 1 or 2), and pharmacologically acceptable salts thereof.

10. A compound having the formula

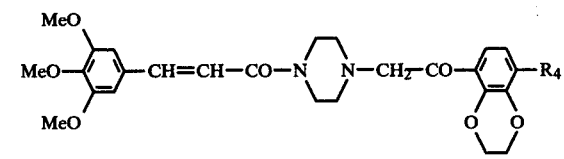

in which R₄ is hydroxy or alkoxy having 1 to 5 carbons, and pharmacologically acceptable salts thereof.

11. A compound according to claim 1 in which X—Ar is

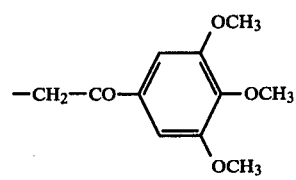

12. A compound according to claim 1 in which X—Ar is

13. A compound according to claim 1 in which X—Ar is

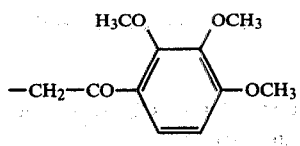

14. A compound according to claim 1 in which X—Ar is

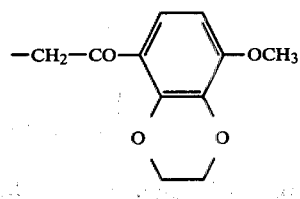

15. A compound according to claim 1 in which X—Ar is

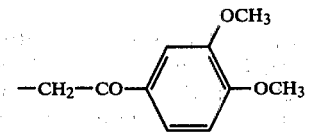

16. A compound according to claim 1 in which X—Ar is

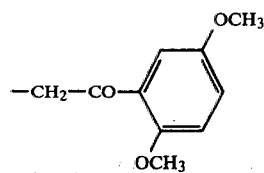

17. A compound according to claim 1 in which X—Ar is

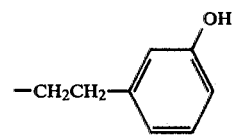

18. A compound according to claim 2 in which X—Ar is

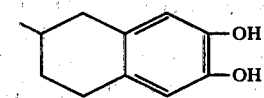

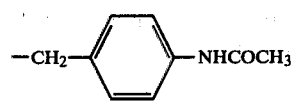

19. A pharmaceutical composition for treating cardiac deficiency which comprises a therapeutically effective amount of a compound as claimed in claim 1, together with a pharmaceutically acceptable vehicle.

20. A method of treating a patient having cardiac deficiency characterized by insufficient cardiac contractile force which comprises administering to that patient a pharmaceutical composition as claimed in claim 19.

* * * * *

UNITED STATES PATENT AND TRADEMARK OFFICE
CERTIFICATE OF CORRECTION

PATENT NO. : 4 368 199
DATED : January 11, 1983
INVENTOR(S) : Jean-Francois R. Ancher et al It is certified that error appears in the above—identified patent and that said Letters Patent is hereby corrected as shown below:

Column 35, line 50; third formula thereon; change to read as follows:

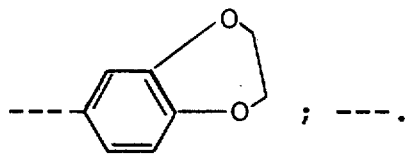

Column 37, line 22; change to read as follows:

--- [2-OCH$_3$, 3,4-diOCH$_3$], [3-OCH$_3$, 4,5-diOCH$_3$], ---.

Signed and Sealed this

Fifth Day of July 1983

[SEAL]

Attest:

GERALD J. MOSSINGHOFF

Attesting Officer     Commissioner of Patents and Trademarks